US008976935B2

(12) United States Patent
Singh et al.

(10) Patent No.: US 8,976,935 B2
(45) Date of Patent: Mar. 10, 2015

(54) COLLIMATOR GRID AND AN ASSOCIATED METHOD OF FABRICATION (71) Applicant: General Electric Company, Schenectady, NY (US)

(72) Inventors: Prabhjot Singh, Guilderland, NY (US); Garth M Nelson, Ballston Lake, NY (US); Brian David Yanoff, Niskayuna, NY (US); Juan Pablo Cilia, Delmar, NY (US)

(73) Assignee: General Electric Company, Niskayuna, NY (US)

( * ) Notice: Subject to any disclaimer, the term of this patent is extended or adjusted under 35 U.S.C. 154(b) by 259 days.

(21) Appl. No.: 13/723,275

(22) Filed: Dec. 21, 2012

(65) Prior Publication Data

US 2014/0177781 A1      Jun. 26, 2014

(51) Int. Cl.
*G21K 1/02* (2006.01)
*G21K 1/00* (2006.01)
*A61B 6/00* (2006.01)

(52) U.S. Cl.
CPC ............... *G21K 1/02* (2013.01); *A61B 6/4291* (2013.01); *A61B 6/4233* (2013.01)
USPC ........ 378/147; 378/149; 378/154; 250/363.1; 250/505.1

(58) Field of Classification Search
CPC ......... G21K 1/025; G21K 1/02; A61B 6/4291
USPC ............. 378/147, 149, 154; 250/363.1, 505.1
See application file for complete search history.

(56) References Cited

U.S. PATENT DOCUMENTS

| | | | |
|---|---|---|---|
| 6,363,136 B1 * | 3/2002 | Flisikowski et al. | 378/154 |
| 6,707,884 B1 * | 3/2004 | Ogawa | 378/154 |
| 6,951,628 B2 | 10/2005 | Eidam et al. | |
| 7,627,089 B2 | 12/2009 | Rantanen | |
| 7,838,856 B2 | 11/2010 | Pinchot | |
| 7,922,923 B2 | 4/2011 | Tang et al. | |
| 8,062,023 B2 | 11/2011 | Appleby et al. | |
| 2009/0039562 A1 | 2/2009 | Freund et al. | |
| 2010/0276829 A1 | 11/2010 | Yang et al. | |
| 2011/0081004 A1 | 4/2011 | Harding et al. | |
| 2011/0189440 A1 | 8/2011 | Appleby et al. | |
| 2012/0069954 A1 * | 3/2012 | Iso et al. | 378/7 |
| 2012/0307963 A1 * | 12/2012 | Watanabe et al. | 378/7 |

OTHER PUBLICATIONS

Makarova et al., "Fabrication of Antiscatter Grids and Collimators for X-Ray and Gamma-Ray Imaging by Lithography and Electroforming", Microsystem Technologies, vol. 14, 2008, pp. 1613-1619.

* cited by examiner

*Primary Examiner* — Nikita Wells
(74) *Attorney, Agent, or Firm* — Robert M. McCarthy (57) ABSTRACT A collimator grid and a method of fabricating the collimator grid are disclosed. The method includes molding a plurality of plates, each plate includes a plurality of grooves in a first surface, a plurality of fin tips in a second surface disposed opposite to the first surface, plurality of ribs on a first pair of peripheral sides, a plurality of first fiducials formed on the plurality of ribs, and a plurality of second fiducials formed on a second pair of peripheral sides. The method includes machining the second surface to form the plurality of fins having predefined dimensions. Further, the method includes stacking the plurality of plates overlapping each other based on the plurality of first fiducials, and machining the plurality of ribs and first fiducials to form the collimator grid.

23 Claims, 10 Drawing Sheets

COLLIMATOR GRID AND AN ASSOCIATED METHOD OF FABRICATION

BACKGROUND

The disclosure relates generally to a detector assembly, and more particularly to a two-dimensional collimator grid, used in a detector assembly of a computed tomography imaging system.

Generally, a computed tomography (herein also referred as "CT") imaging system is utilized for a wide variety of imaging applications, such as medical imaging, and non-medical industrial imaging. In the medical imaging domain, for example, the CT imaging system is generally configured to transmit x-ray beams through a structure, such as a human body, to detect and diagnose abnormalities, such as tumors. The x-ray beams are subsequently received and processed in the CT imaging system to generate a three-dimensional image of the body structure that can be analyzed by clinicians as a diagnostic aid.

Typically, the CT imaging system includes an image detector assembly for receiving x-ray beams passed through the human body. The image detector assembly includes a collimator grid designed to reduce x-ray beams scatter and also to shield the underlying components of the image detector assembly from undesirable exposure. Currently, collimator grids are two-dimensional (herein also referred as "2D") arrays that are assembled from thin, and long metal blades and fins, such as tungsten blades, and intersecting fins that are approximately perpendicular to a body of each blade. The process of assembling a 2D collimator requires many repetitive steps, and the cost of assembling the collimator may increase the overall cost of the image detector assembly. Further, the current 2D collimator design is not easily extended to a wider range of image detectors because of the mechanical stability of the blades in the collimator, particularly under the conditions of high centripetal acceleration encountered in a rotating CT imaging system.

BRIEF DESCRIPTION

In accordance with one exemplary embodiment, a method of molding a collimator grid is disclosed. The method includes molding a plurality of plates. Each plate among the plurality of plates includes a plurality of grooves formed in a first surface, and a plurality of fin tips in a second surface disposed opposite to the first surface, each fin tip is aligned with the corresponding groove. Further, each plate includes a plurality of ribs formed on a first pair of peripheral sides, a plurality of first fiducials spaced apart from each other and formed on the plurality of ribs, and a plurality of second fiducials formed on a second pair of peripheral sides. The method includes machining the second surface of each plate, between the fin tips, to form the plurality of fins having predefined dimensions. Further, the method includes stacking the plurality of plates overlapping each other based on the plurality of fiducials such that the plurality of fins of each plate are coupled to the machining the plurality of ribs and the plurality of grooves of the corresponding adjacent plate and machining the plurality of ribs and the first fiducials to form the collimator grid.

In accordance with another exemplary embodiment, a collimator grid is disclosed. The collimator grid includes a plurality of plates stacked overlapping each other. Each plate among the plurality of plates includes a first surface having a plurality of grooves and a second surface having a plurality of fins aligned with the plurality of grooves. The plurality of fins of each plate are coupled to the plurality of grooves of the corresponding adjacent plate. The plurality of fins of each plate includes a center fin oriented perpendicular to a blade portion of each plate and a remaining number of fins oriented perpendicular to the blade portion and inclined towards the center fin.

In accordance with yet another embodiment, a computed tomography imaging system is disclosed. The computed tomography (herein also referred as "CT") imaging system includes an x-ray source, and an image detector assembly, which is disposed facing the x-ray source. The imaging detector assembly includes a collimator grid. The collimator grid includes a plurality of plates stacked overlapping each other. Each plate among the plurality of plates includes a first surface having a plurality of grooves and a second surface having a plurality of fins aligned with the plurality of grooves. The plurality of fins of each plate are coupled to the plurality of grooves of the corresponding adjacent plate. The plurality of fins of each plate includes a center fin oriented perpendicular to a blade portion of each plate and a remaining number of fins oriented perpendicular to the blade portion and inclined towards the center fin.

DRAWINGS

These and other features and aspects of embodiments of the present invention will become better understood when the following detailed description is read with reference to the accompanying drawings in which like characters represent like parts throughout the drawings, wherein.

DETAILED DESCRIPTION

While only certain features of embodiments of the invention have been illustrated and described herein, many modifications and changes will occur to those skilled in the art. It is, therefore, to be understood that the appended claims are intended to cover all such modifications and changes as fall within the true spirit of the invention.

Embodiments herein disclose an image detector assembly used in a computed tomography (herein also referred as a "CT") imaging system. More particularly, certain embodiments of the present invention disclose a method of fabricating a collimator grid, which is used in the image detector assembly of the CT imaging system. In accordance with one exemplary embodiment of the present invention, the method of fabricating a collimator grid includes molding a plurality of plates having a plurality of ribs, fin tips, grooves, and fiducials. Further, the method includes machining the plurality of fins to predefined dimensions, in each plate, and stacking each plate among the plurality of plates overlapping each other. The method includes coupling a pair of brackets to the stacked plurality of plates, and then machining the stacked plurality of plates coupled to the pair of brackets, to remove a plurality of ribs and fiducials to form a collimator grid. Alternatively, the method includes machining the stacked plurality of plates to remove the plurality of ribs and fiducials to form the collimator grid.

More specifically, certain embodiments of the present system disclose a method for fabricating a collimator grid, which is used in the image detector assembly. The method includes molding a plurality of plates having one or more features. Each plate includes a plurality of grooves formed in a first surface, a plurality of fin tips formed in a second surface disposed opposite to the first surface. The plurality of plates include a plurality of ribs formed on a first pair of peripheral sides, a plurality of first fiducials spaced apart from each other and formed on the plurality of ribs, and a plurality of second fiducials formed on a second pair of peripheral sides. Further, the method includes machining the second surface of each plate, between the fin tips to form the plurality of fins having predefined dimensions in each molded plate. The method further includes stacking the plurality of plates overlapping each other so as to couple the plurality of fins of each plate to the plurality of grooves of the corresponding adjacent plate. Further, the method includes coupling a pair of brackets to the plurality of stacked plates via the second fiducials formed on the second pair of peripheral sides of each plate. Finally, the method includes machining the plurality of ribs and the plurality of first fiducials of the stacked plates to form the collimator grid. Alternatively, the method further includes machining the plurality of ribs and the plurality of first fiducials of the stacked plates to form the collimator grid.

Figure 1:
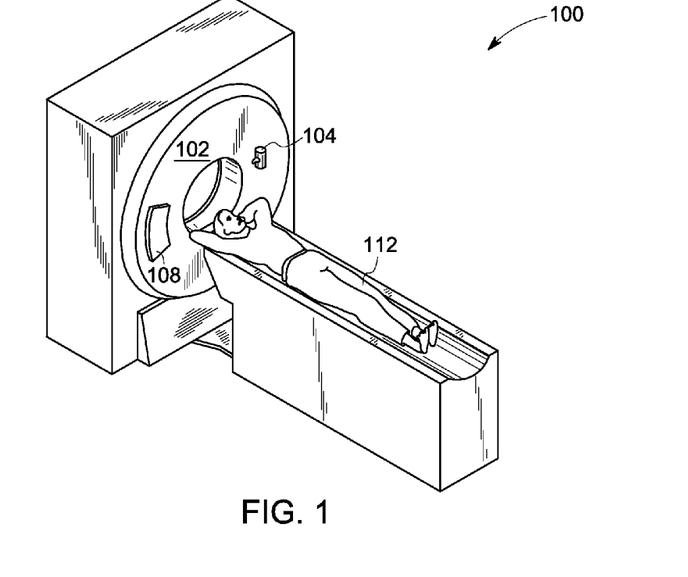
FIG. 1 is an illustration of a computed tomography imaging system having an image detector assembly, and an x-ray source in accordance with one exemplary embodiment.

FIG. 1 illustrates a perspective view of a computed tomography (herein also referred as a "CT") imaging system 100 in accordance with one exemplary embodiment. In the illustrated embodiment, the CT imaging system 100 includes a scanner assembly 102 as a gantry assembly, an x-ray source 104, and an image detector assembly 108. The scanner assembly 102 is used for scanning a structure for example, a medical patient 112. Although a particular type of CT imaging system 100 having a specific type of an image detector assembly 108 in the scanner assembly 102 is illustrated, other possible varieties of CT imagining system 100 having different types of image detector assembly are also envisioned.

Figure 2:
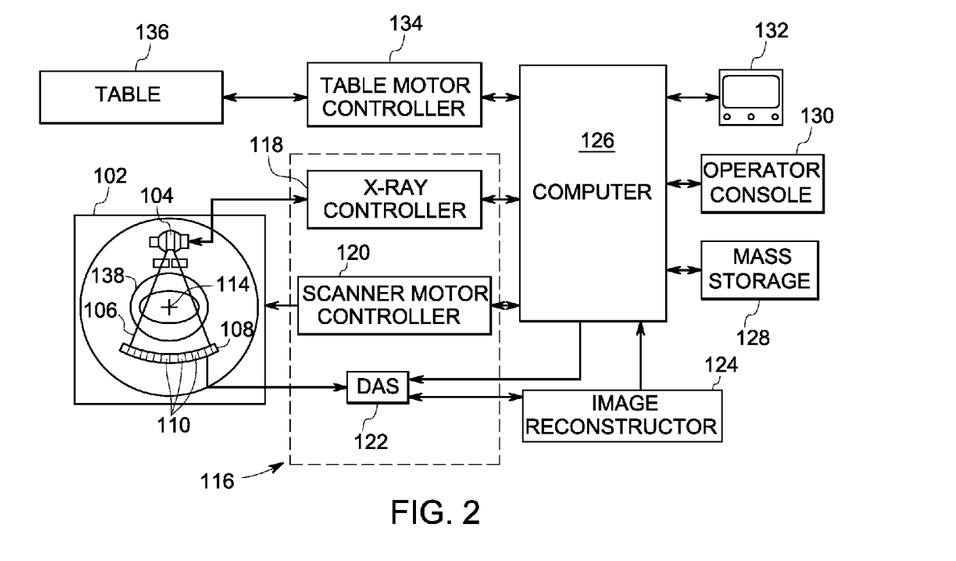
FIG. 2 is a block diagram of the imaging system illustrated in FIG. 1 in accordance with one exemplary embodiment.

Now referring to FIG. 2, a block diagram of the CT system is disclosed. The x-ray source 104 is used for projecting x-ray beams 106 toward the image detector assembly 108, which is positioned opposite the x-ray source 104. The image detector assembly 108 includes a plurality of detector elements arranged to form a detector array 110. In one embodiment, the detector array 110 may be a photo-detector array. Each of the detector elements are configured to sense the x-ray beams 106 passing through a structure, such as the medical patient 112, and produce analog data representing an intensity of the x-ray beams 106 as it passes through the medical patient 112. Commonly, during a scanning process for gathering the x-ray beams 106, the scanner assembly 102 may be rotated about a center of rotation 114. The rotation of the scanner assembly 102 and the operation of the x-ray source 104 are preferably governed by a control unit 116.

In the illustrated embodiment, the control unit 116 includes an x-ray controller 118, a scanner motor controller 120, and a data acquisition system (herein also referred as a "DAS") 122. In one example, the control unit 116 preferably includes the x-ray controller 118 for providing a timing signal to the x-ray source 104, and the scanner motor controller 120 for controlling the rotational speed, and position of the scanner assembly 102. The detector array 110 receives the x-ray beams 106, and passes the analog data representative of a scanned image, to the DAS 122. The DAS 122 samples the analog data from the detector array 110, and converts the analog data to digital data for subsequent processing. An image re-constructor 124 receives sampled and digitized x-ray data from DAS 122 and performs high speed image reconstruction. The reconstructed image is applied as an input to a computer 126 which stores the image in a mass storage device 128.

The computer 126 also receives commands and scanning parameters from an operator via an operator console 130 that has a keyboard or similar input device. An associated display 132 allows the operator to observe the reconstructed image and other data from the computer 126. The operator supplied commands and parameters are used by computer 126 to provide control signals and information to the DAS 122, the x-ray controller 118, and the scanner motor controller 120. In addition, the computer 126 operates a table motor controller 134 which controls a motorized table 136 to position the patient within the scanner assembly 102. Particularly, the table 136 moves portion of the patient through a scanner opening 138.

Figure 3:
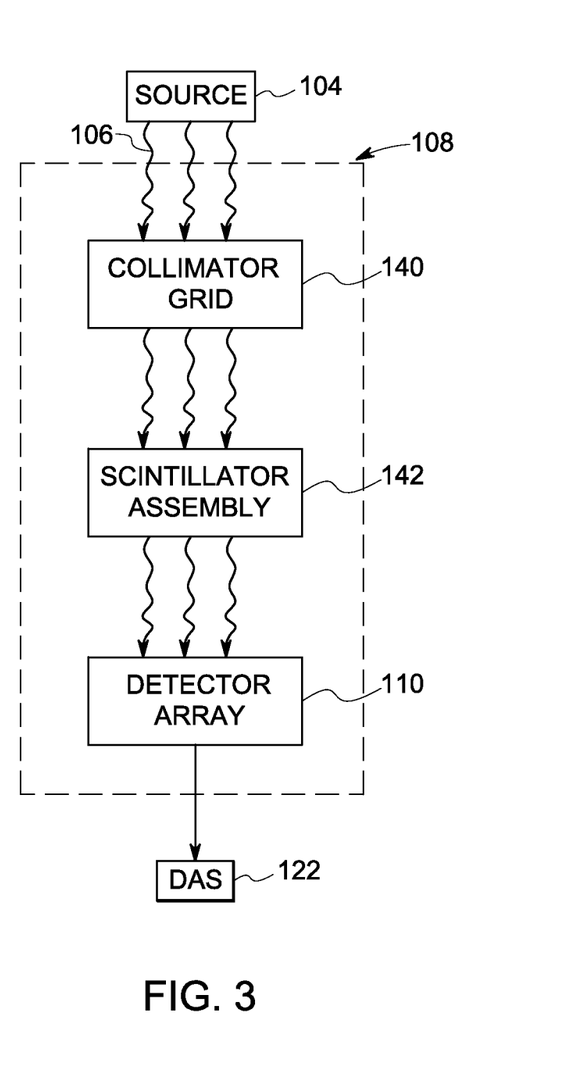
FIG. 3 is a simplified block diagram of the image detector assembly of FIG. 2 in accordance with one exemplary embodiment.

FIG. 3 illustrates a block diagram of the image detector assembly 108 in accordance with one exemplary embodiment. As described herein, the image detector assembly 108 receives x-ray beams 106 from the x-ray source 104 and transmits analog data to the DAS 122. The image detector assembly 108 includes a collimator grid 140, a scintillator assembly 142 and the detector array 110. During operation, x-ray beams 106 pass through an object such as the patient, then through the openings or slits in the collimator grid 140, and are subsequently received by the detector array 110. The collimator grid 140 is generally configured to limit and define the direction and angular divergence of the x-ray beams 106 onto the scintillator assembly 142. In accordance with embodiments of the present invention, the collimator grid 140 includes a two dimensional collimator array made of radiation absorbent material such as a tungsten-loaded polymer, a tungsten metal, a tungsten alloy, a molybdenum-loaded polymer, a molybdenum metal, molybdenum alloy, a lead metal, and a lead bearing alloy, for example. The x-ray beams 106 are directed through the collimator grid 140 to the scintillator assembly 142. The scintillator assembly 142 is configured to convert the x-ray beams 106 into light for detection by the underlying detector array 110. The detector array 110 typically includes a number of photo detectors, such as photodiodes. The photodiodes in the detector array 110 sense the light rays from the scintillator assembly 142 and convert the light rays into analog data which are then transmitted to the DAS 122, which converts the analog data to digital data for subsequent processing.

Figure 4A:
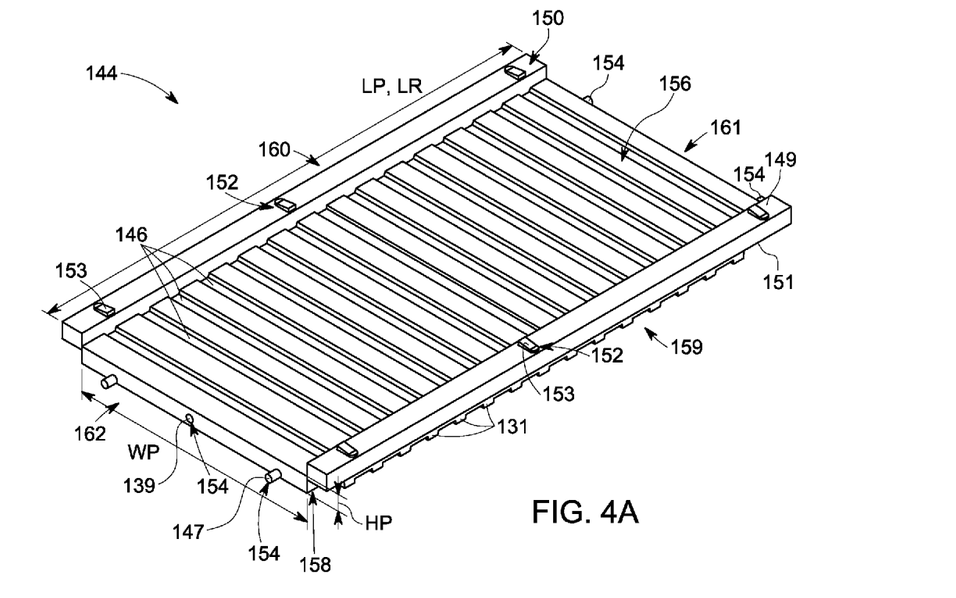
FIG. 4a is a perspective view of a molded plate having a plurality of grooves, fin tips, ribs, first fiducials, and second fiducials in accordance with one exemplary embodiment.

FIG. 4a illustrates a perspective view of a molded plate 144 in accordance with one exemplary embodiment. The molded plate 144 includes a plurality of grooves 146, a plurality of fin tips 131, a plurality of ribs 150, a plurality of first fiducials 152, and a plurality of second fiducials 154.

The plate 144 may be produced using a process such as but not limited to compression molding or injection molding. The raw material used for molding the plate 144 may include but not limited to graphite material, sand material, and the like. The raw material may vary depending on the application and design criteria. In certain embodiments, the plate 144 is casted from materials including at least one of a tungsten-loaded polymer, a tungsten metal, a tungsten alloy, a molybdenum-loaded polymer, a molybdenum metal, a molybdenum alloy, a lead metal, and a lead bearing alloy. It should be noted herein that a plurality of such plates 144 are formed by molding as discussed herein.

In the illustrated embodiment, the plate 144 has a rectangular shape. The shape of the plate 144 may vary depending on an application and design criteria. In the illustrated embodiment, the plate 144 includes a first surface 156, a second surface 158, a first pair of peripheral sides 159, 160, and a second pair of peripheral sides 161, 162. In one embodiment, the height "HP" of the plate 144 is generally in the range of about 15 mm to about 30 mm, for example. The width "WP" of the plate 144 may be in the range of approximately 60 mm to 80 mm, for example. Similarly, the length "LP" of the plate 144 may be in the range of approximately 130 mm to 180 mm, for example. The dimensions of the plate 144 discussed herein should not be construed as a limitation of the present invention. The plate 144 may be molded to any other dimensions based on the application and design criteria.

In one embodiment, a plurality of grooves 146 are formed in the first surface 156 of the plate 144 by molding. In an alternative exemplary embodiment, the plurality of grooves 146 are formed in each plate 144 by machining. In certain other embodiments, the first surface 156 may be interchangeable with the second surface 158 of the plate 144. In the illustrated embodiment, the plurality of grooves 146 are formed parallel to each other and the shape of each groove 146 tapers from one end towards another end. In one example, the plurality of grooves 146 have a dove tail shaped cross-section. In another example, the plurality of grooves 146 have a semi-circular cross-section. In certain other embodiments, the shape of the plurality of grooves 146 may vary depending on the application and design criteria. Each groove among the plurality of grooves 146 are aligned with the corresponding fin tips among the plurality of fin tips 131 formed on the second surface 158 disposed opposite to the first surface 156 of the plate 144. In the illustrated embodiment, the plurality of fin tips 131 are formed in the second surface 158 of the plate 144 by a molding process. The shape of each fin tip among the plurality of fin tips 131 are tapered from one end towards another end. In certain other embodiments, the shape of the plurality of fin tips 131 may vary depending on the application and design criteria. In an alternative exemplary embodiment, the plurality of fin tips 131 are formed in the second surface 158 of each plate 144 by machining.

The plurality of ribs 150 are formed in the first pair of peripheral sides 159, 160 of the plate 144. The plurality of ribs 150 are designed to provide stiffness to the plate 144. In the illustrated embodiment, one rib 150 is provided on each side among the first pair of peripheral sides 159, 160 of the plate 144. The plurality of ribs 150 are rectangular shaped and protrudes outward from the first pair of peripheral sides 159, 160. The length "LR" of the plurality of ribs 150 extends along the length "LP" of the plate 144. In another embodiment, the shape and dimensions of the plurality of ribs 150 may vary depending on the application and design criteria.

In one embodiment, the plurality of first fiducials 152 are spaced apart from each other and formed on a first rib surface 149 and on a second rib surface 151 of each rib 150. In the illustrated embodiment, the plurality of first fiducials 152 include a plurality of protrusions 153. The plurality of first fiducials 152 are used for aligning the plurality of plates 144 during stacking process discussed in greater detail below.

The plurality of second fiducials 154 are formed on the second pair of peripheral sides 161, 162 of the plate 144. The second fiducials 154 may include at least one of a plurality of recesses 139, and protrusions 147. The plurality of second fiducials 154 are disposed spaced apart from each other on the second pair of the peripheral sides 161, 162 of the plate 144. It should be noted herein that the terms "second fiducials" and "first interlocking fiducials" may be used interchangeably. The plurality of second fiducials 154 are designed to be coupled to a pair of brackets discussed in greater detail below.

Figure 4B:
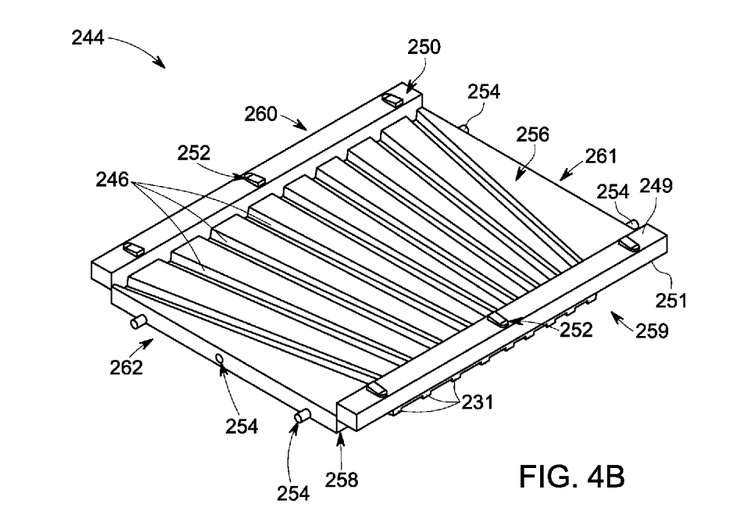
FIG. 4b is a perspective view of a molded plate having a plurality of grooves, fin tips, ribs, first fiducials, and second fiducials in accordance with another exemplary embodiment.

FIG. 4b illustrates a perspective view of a molded plate 244 in accordance with one exemplary embodiment. The molded plate 244 includes a plurality of grooves 246, a plurality of fin tips 231, a plurality of ribs 250, a plurality of first fiducials 252, and a plurality of second fiducials 254.

In the illustrated embodiment, the plurality of grooves 246 are molded on a first surface 256 of the plate 244. The plurality of grooves 256 are inclined from one first peripheral side 259 to another first peripheral side 260 of the plate 244. The plurality of fin tips 231 are formed in a second surface 258 of the plate 244 by molding process. The plurality of fin tips 231 are also inclined from one first peripheral side 259 to another first peripheral side 260 of the plate 244. Each groove among the plurality of grooves 246 are aligned with the corresponding fin tip among the plurality of fin tips 231. The plurality of ribs 250 are formed in the first pair of peripheral sides 259, 260 of the plate 244. The plurality of first fiducials 252 are spaced apart from each other and formed on a first rib surface 249 and on a second rib surface 251 of each rib 250.

The plurality of second fiducials 254 are formed on a second pair of peripheral sides 261, 262 of the plate 244.

Figure 5A:
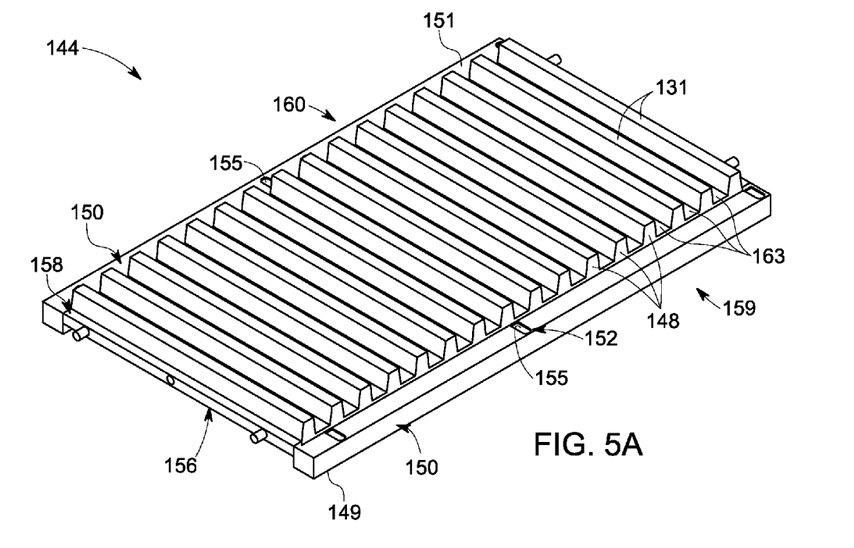
FIG. 5a is a perspective view of a molded plate after machining the material between each fin tip, having a plurality of fins, ribs, first fiducials, and second fiducials in accordance with one exemplary embodiment.

Referring to FIG. 5a, a perspective view of the molded plate 144 of the collimator grid in accordance with an exemplary embodiment of FIG. 4a is disclosed. In certain embodiments, the second surface 158 of the plate 144 is machined to form a plurality of recesses 163 so as to form a plurality of fins 148. In such embodiments, each recess among the plurality of recesses 163 is formed between the mutually adjacent fins 148. The second surface 158 of the plate 144 is machined between the mutually adjacent fin tips 131 to form recesses 163 and thereby form fins 148 having predefined dimensions. In the illustrated embodiment, each fin among the plurality of fins 146 are parallel to each other and the shape of each fin among the plurality of fins 148 is tapered from one end towards another end. In one example, the plurality of fins 148 have a dove tail shaped cross-section. In another example, the plurality of fins 148 have a semi-circular cross-section. In certain other embodiments, the shape of the plurality of fins 148 may vary depending on the application and design criteria. Each fin among the plurality of fins 148 is aligned with the corresponding adjacent plurality of grooves 146 (shown in FIG. 4a) formed on the first surface 156 of the plate 144. In the illustrated embodiment, the plurality of first fiducials 152 includes a plurality of recesses 155 formed on the second rib surface 151 of each rib 150.

Figure 5B:
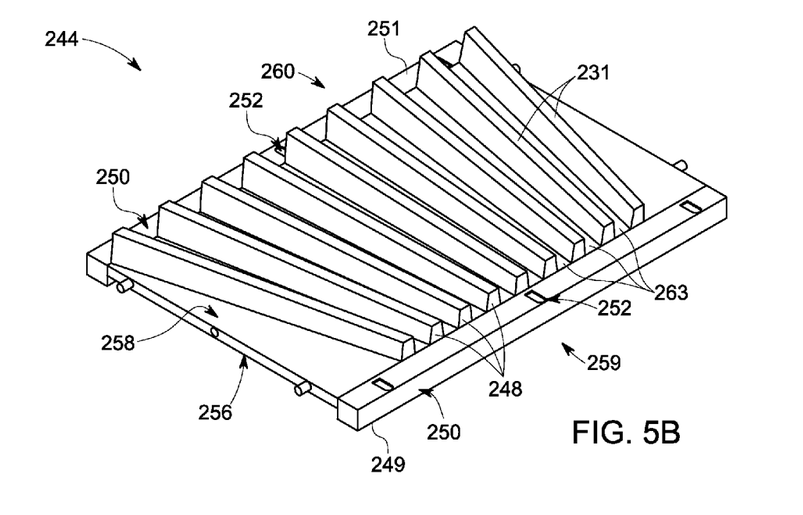
FIG. 5b is a perspective view of a molded plate after machining the material between each fin tip, having a plurality of fins, ribs, first fiducials, and second fiducials in accordance with another exemplary embodiment.

Referring to FIG. 5b, a perspective view of the molded plate 244 of the collimator grid in accordance with an exemplary embodiment of FIG. 4b is disclosed. In certain embodiments, the second surface 258 of the plate 244 is machined to form a plurality of recesses 263 so as to form a plurality of fins 248. In such embodiments, each recess among the plurality of recesses 263 is formed between the mutually adjacent fins 248. In the illustrated embodiment, each fin among the plurality of fins 246 is inclined from one first peripheral side 259 to another first peripheral side 260 of the plate 244. Each fin among the plurality of fins 248 is aligned with the corresponding adjacent plurality of grooves 246 (shown in FIG. 4b) formed on the first surface 256 of the plate 244. Similarly, the height of each fin 248 is gradually increased from one first peripheral side 259 to another first peripheral side 260.

Figure 6A:
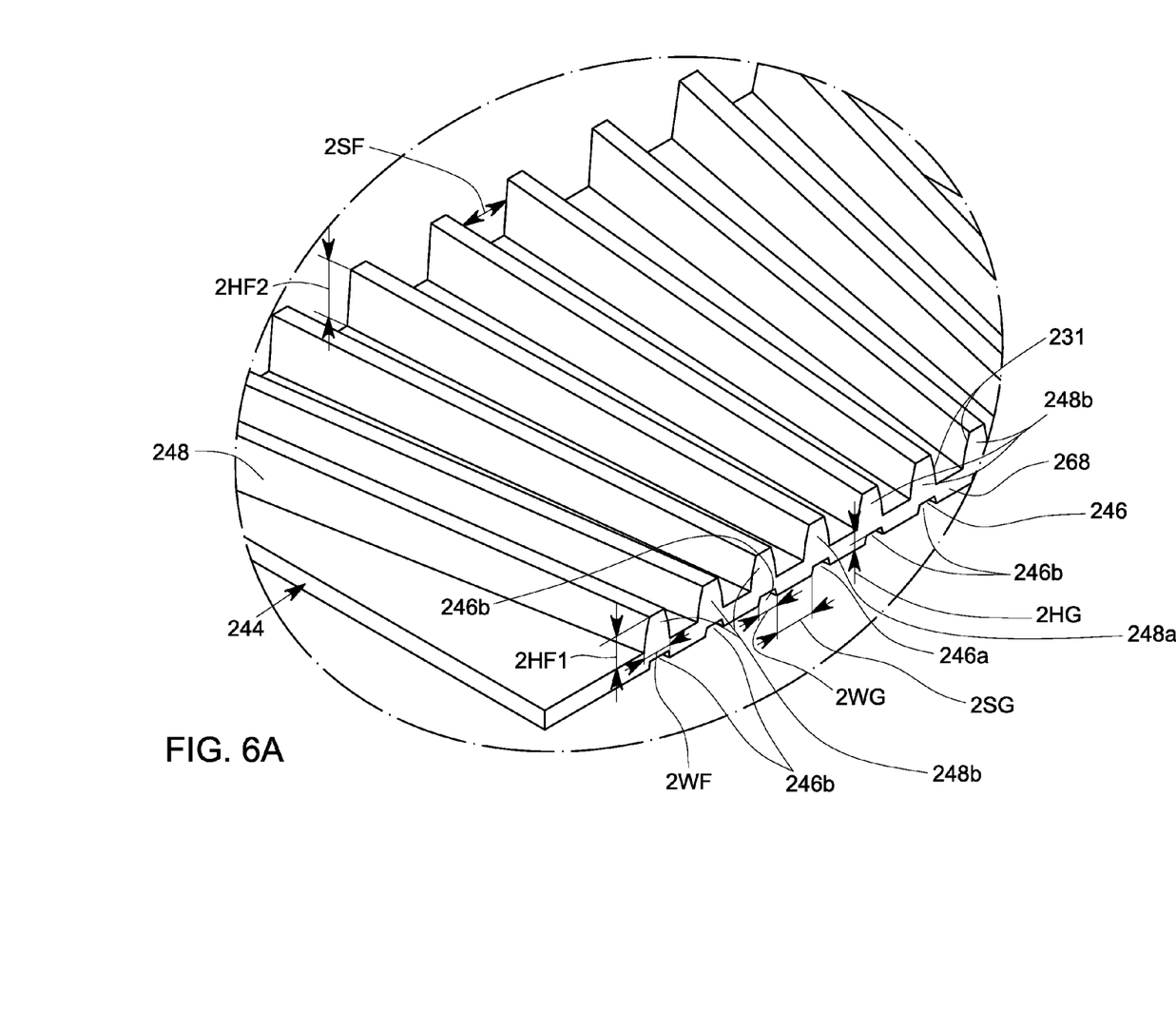
FIG. 6a is a perspective view illustrating the orientation of a plurality of fins and a plurality of grooves in the plate in accordance with one exemplary embodiment.

FIG. 6a is a partial perspective view of the plurality of fins 248 and the plurality of grooves 246 in the plate 244 in accordance with an embodiment of FIG. 5b. In the illustrated embodiment, a center fin 248a among the plurality of fins 248 is formed perpendicular to a blade portion 268 of the plate 244. The remaining fins 248b among the plurality of fins 248 are oriented perpendicular to the blade portion 268, and inclined from one first peripheral side 259 to another first peripheral side 260 towards the center fin 248a. Specifically, each of the remaining fins 248b may be inclined at an angle of less than or equal to twenty degrees with respect to the perpendicular orientation of the blade portion 268. The plurality of fins 248a, 248b are designed to focally align with the x-ray source. Similarly, in the illustrated embodiment, a center groove 246a among the plurality of grooves 246 is formed perpendicular to the blade portion 268 of the plate 244. The remaining grooves 246b among the plurality of grooves 246 are oriented perpendicular to the blade portion 268, and inclined from one first peripheral side 259 to another first peripheral side 260 towards the center groove 246a. Specifically, each of the remaining grooves 246b is oriented at an angle of less than or equal to twenty degrees with respect to the perpendicular orientation of the center groove 246a. The plurality of grooves 246a, 246b are also designed to focally align with the x-ray source.

In the illustrated embodiment, the height "2HG" of the plurality of grooves 246a, 246b is in the range of about 50 microns and 100 microns, for example. The spacing "2SG" between each groove among the plurality of grooves 246a, 246b may be in the range of approximately 0.4 mm to 3.0 mm, for example. Similarly, the width "2WG" of each groove among the plurality of grooves 246a, 246b may be in the range of approximately 50 microns to 100 microns, for example. The dimensions of each groove discussed herein should not be construed as a limitation of the present invention.

In the illustrated embodiment, the height of the plurality of fins 248 is gradually increased from one first peripheral side 259 to another first peripheral side 260. The height "2HF1" of the plurality of fins 248a, 248b at one first peripheral side 259 is typically in the range of about 1.0 mm and 1.2 mm, for example. Similarly, the height "2HF2" of the plurality of fins 248a, 248b at another first peripheral side 260 is typically in the range of about 1.3 mm and 1.5 mm, for example. The spacing "2SF" between each fin among the plurality of fins 248a, 248b may be in the range of approximately 0.4 mm to 3.0 mm, for example. Similarly, the width "2WF" of each fin among the plurality of fins 248a, 248b may be in the range of approximately 50 microns to 100 microns, for example. The dimensions of each fin mentioned above should not be construed as a limitation of the present invention.

Figure 6B:
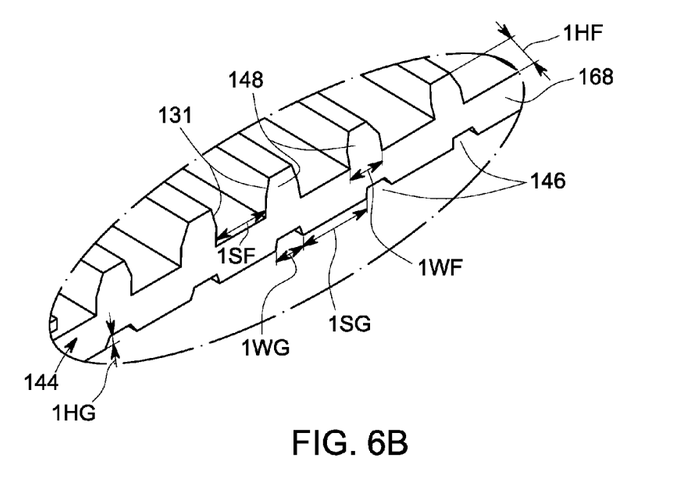
FIG. 6b is a perspective view illustrating the orientation of a plurality of fins and a plurality of grooves in the plate in accordance with another exemplary embodiment.

FIG. 6b is a partial perspective view of the plurality of fins 148 and the plurality of grooves 146 in the plate 144 in accordance with an embodiment of FIG. 5a. In the illustrated embodiment, the height "1HG" of the plurality of grooves 146 is in the range of about 50 microns and 100 microns, for example. The spacing "1SG" between the plurality of grooves 146 may be in the range of approximately 0.4 mm to 3.0 mm, for example. Similarly, the width "1WG" of each groove among the plurality of grooves 146 may be in the range of approximately 50 microns to 100 microns, for example. The dimensions of each groove discussed herein should not be construed as a limitation of the present invention.

In the illustrated embodiment, the height "1HF" of the plurality of fins 148 is typically in the range of about 1.0 mm and 1.2 mm, for example. The spacing "1 SF" between each fin among the plurality of fins 148 may be in the range of approximately 0.4 mm to 3.0 mm, for example. Similarly, the width "1WF" of each fin among the plurality of fins 148a, 148b may be in the range of approximately 50 microns to 100 microns, for example. The dimensions of each fin mentioned above should not be construed as a limitation of the present invention.

Figure 7:
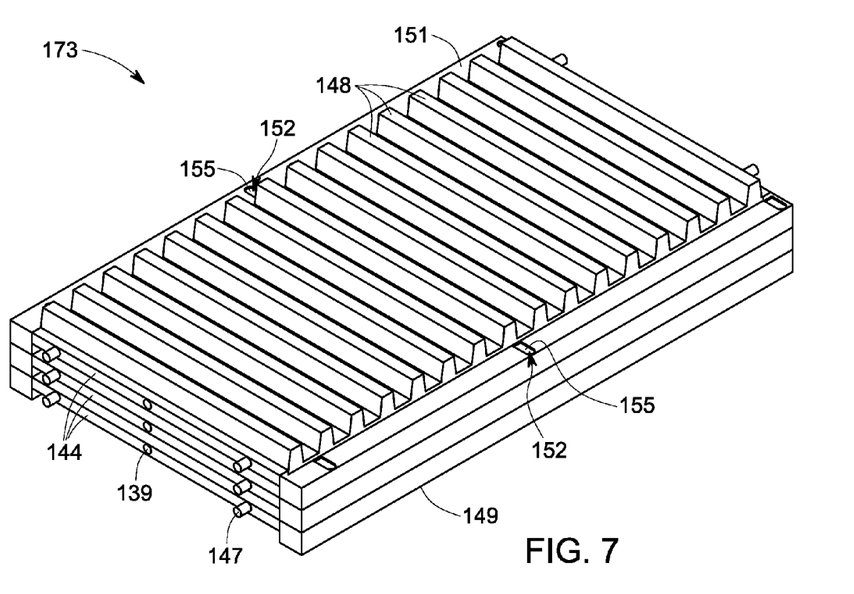
FIG. 7 is a perspective view of a plurality of plates stacked overlapping each other in accordance with one exemplary embodiment.

FIG. 7 illustrates a perspective view of a stacked assembly 173 of the plurality of plates overlapping each other in accordance with one exemplary embodiment. In the illustrated embodiment, the plates 144 are stacked one above the other overlapping each other. The plurality of first fiducials 152 i.e. protrusion (refer FIG. 4a), recesses 155 are used to align the plates 144 one above the other. During stacking of the plates 144, the plurality of protrusions of the first fiducials 152 of each plate 144 are coupled to the corresponding recesses 155 of the plurality of first fiducials 152 of the adjacent plate 144. The plates 144 are stacked in such a way that each fin among the plurality of fins 148 of each plate 144 are coupled to the corresponding groove among the plurality of grooves 146 (refer FIG. 4a) of the adjacent plate 144. In the illustrated embodiment, three plates 144 are stacked to form the stacked assembly 173. In some other embodiments, the number of plates 144 may vary based on the application and design criteria. The first fiducials 152 i.e. protrusion 153 (refer FIG.

4a), recesses 155 acts the alignment fiducials to perfectly stack the plate's one above the other.

Figure 8A:
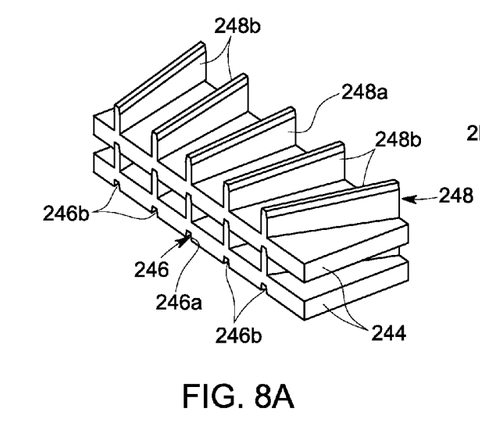
FIG. 8a is a perspective view illustrating the orientation of a plurality of fins and a plurality of grooves of a plurality of plates stacked overlapping each other in accordance with another exemplary embodiment.

FIG. 8a illustrates a perspective view of the plurality of fins 248 and the plurality of grooves 246 of the plurality of plates 244 stacked overlapping each other in accordance with an exemplary embodiment of FIG. 6a. In the illustrated embodiment, the remaining fins 248b, and the center fin 248a of the plate 244 are coupled to the remaining grooves 246b, and the center groove 246a respectively of the corresponding adjacent plate 244. The inclination of the remaining fins 248b as discussed herein facilitates to provide a good focal alignment with the x-ray source.

Figure 8B:
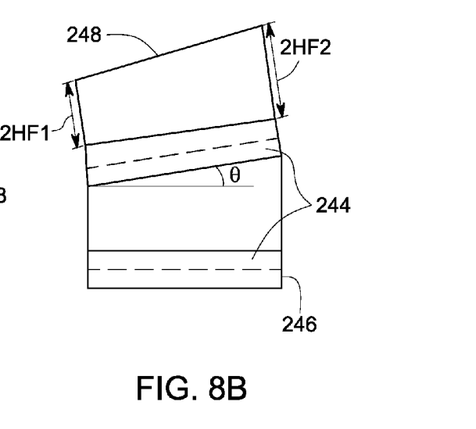
FIG. 8b is a side view illustrating the orientation of a plurality of fins and a plurality of grooves of a plurality of plates stacked overlapping each other in accordance with another exemplary embodiment.

FIG. 8b illustrates a side view of the plurality of fins 248, and the plurality of grooves 246 of the plurality of plates 244 stacked overlapping each other in accordance with an exemplary embodiment of FIG. 8a. The heights "2HF1", "2HF2" of the corresponding fins 248 are varied such that the plurality of plates 244 are inclined at an angle "θ", thus enabling the collimator gird to be focally aligned with the x-ray source.

Figure 9A:
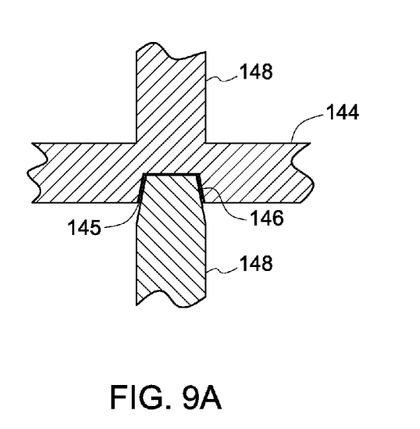
FIG. 9a is a sectional view of a fin coupled to a groove in accordance with one exemplary embodiment.

FIG. 9a illustrates a sectional view of the fin 148 of one plate 144 coupled to the corresponding groove 146 of the adjacent plate 144 in accordance with an exemplary embodiment of FIG. 7. In some embodiments, the fin 148 is further bonded to the groove 146 using an adhesive 145. In some other embodiments, the fin 148 is further bonded to the groove 146 using mechanical joining techniques, such as an ultrasound welding. The bonding techniques discussed herein should not be construed as a limitation of the present invention. In the illustrated embodiment, the groove 146 and the fin 148 have a dove tail shaped cross-section.

Figure 9B:
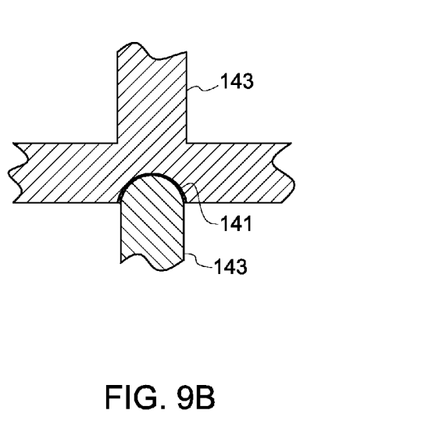
FIG. 9b is a sectional view of a fin coupled to a groove in accordance with another exemplary embodiment.

FIG. 9b illustrates a sectional view of a fin 143 of one plate coupled to the corresponding groove 141 of the adjacent plate in accordance with another exemplary embodiment. The fin 143 and the groove 141 have a semi-circular cross-section.

Figure 10:
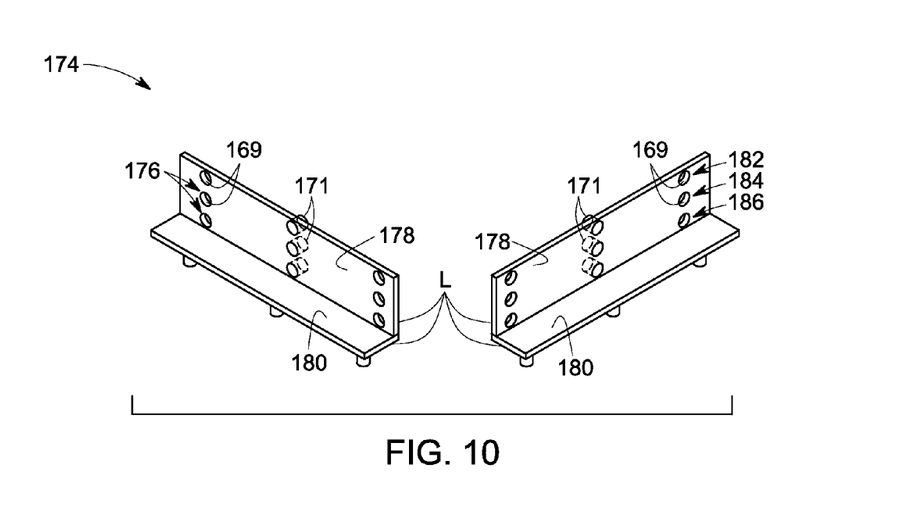
FIG. 10 is a perspective view of a pair of brackets in accordance with one exemplary embodiment.

FIG. 10 is a perspective view of a pair of brackets 174 in accordance with one exemplary embodiment of the present invention. In the illustrated embodiment, each bracket 174 has an L shape and includes a plurality of third fiducials 176. The pair of brackets 174 may be designed to any other shapes based on the need of the application and design criteria. The L shaped bracket includes a side wall 178 and a mounting plate 180. In one embodiment, the side wall 178 includes the plurality of third fiducials 176. The plurality of third fiducials 176 includes at least one of a plurality of recesses 169, and protrusions 171. The plurality of third fiducials 176 are disposed spaced apart from each other on the side wall 178. In this example, the plurality of third fiducials 176 are formed in one or more rows on the side wall 178. The number of rows of the plurality of third fiducials 176 in the bracket 174 is based on the number of plates stacked in the stacked assembly. In the illustrated embodiment, there are three rows 182, 184, 186 of the plurality of third fiducials 176. The plurality of third fiducials 176 formed on the bracket 174 are designed to be aligned with the plurality of second fiducials formed on the plate. It should be noted herein that the terms "third fiducials" and "second interlocking fiducials" may be used interchangeably.

Figure 11A:
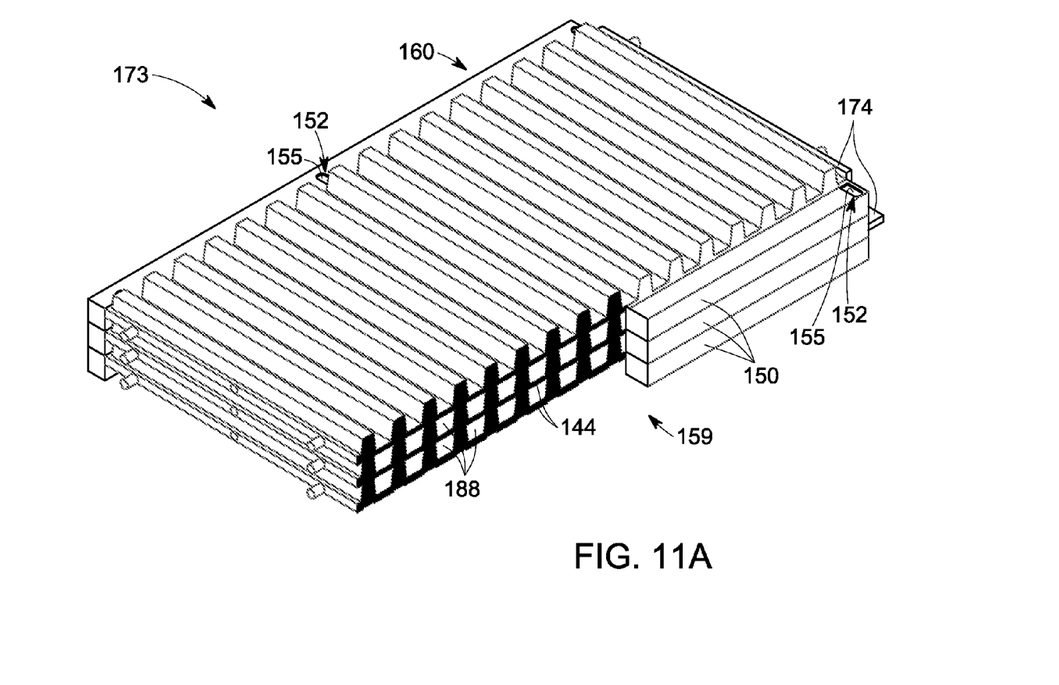
FIG. 11a is a perspective view of partially machined plurality of stacked plates in accordance with one exemplary embodiment.

FIG. 11a is a perspective view of partially machined stacked assembly 173, in accordance with an exemplary embodiment of FIG. 7. The stacked assembly 173 may be mounted on machining equipment (not illustrated) to remove the plurality of ribs 150 having the plurality of first fiducials 152 i.e. recesses 155 and protrusion from the first pair of the peripheral sides 159, 160 of the plurality of plates 144. In the illustrated embodiment, the plurality of ribs 150 with the plurality of first fiducials 152 i.e. recesses 155 are shown partially removed from the stacked assembly 173 to form a plurality of slits 188 in the stacked assembly 173.

Figure 11B:
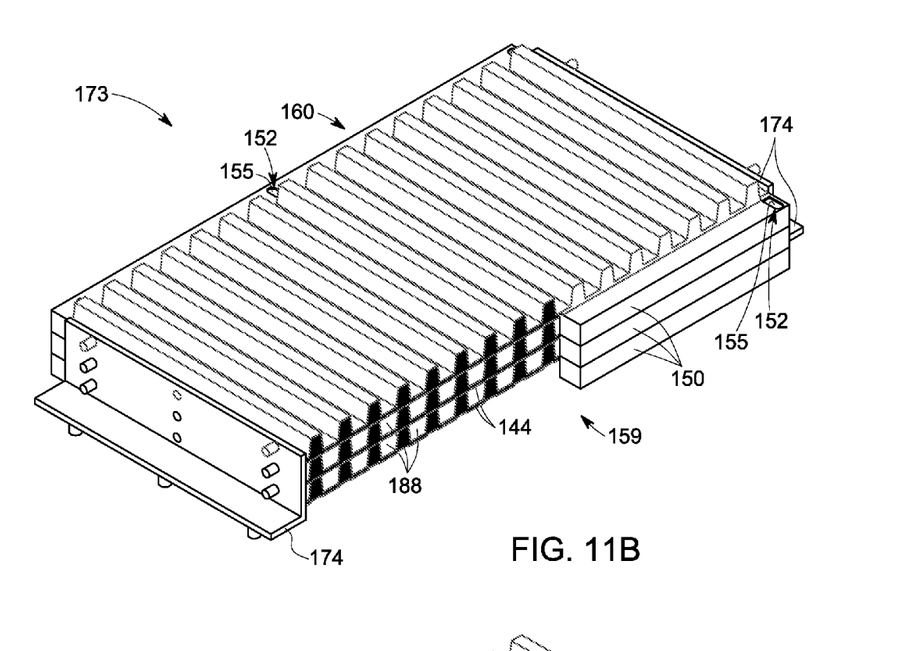
FIG. 11b is a perspective view of partially machined plurality of stacked plates coupled to a pair of brackets in accordance with another exemplary embodiment.

FIG. 11b is a perspective view of partially machined stacked assembly 173 coupled with the pair of brackets 174, in accordance with an exemplary embodiment of FIGS. 7 and 10. The stacked assembly 173 may be machined to remove the plurality of ribs 150 having the plurality of first fiducials 152 i.e. recesses 155 and protrusions from the first pair of the peripheral sides 159, 160 of the plurality of plates 144. In the illustrated embodiment, the plurality of ribs 150 with the plurality of first fiducials 152 are shown partially removed from the stacked assembly 173 to form a plurality of slits 188 in the stacked assembly 173.

Figure 12:
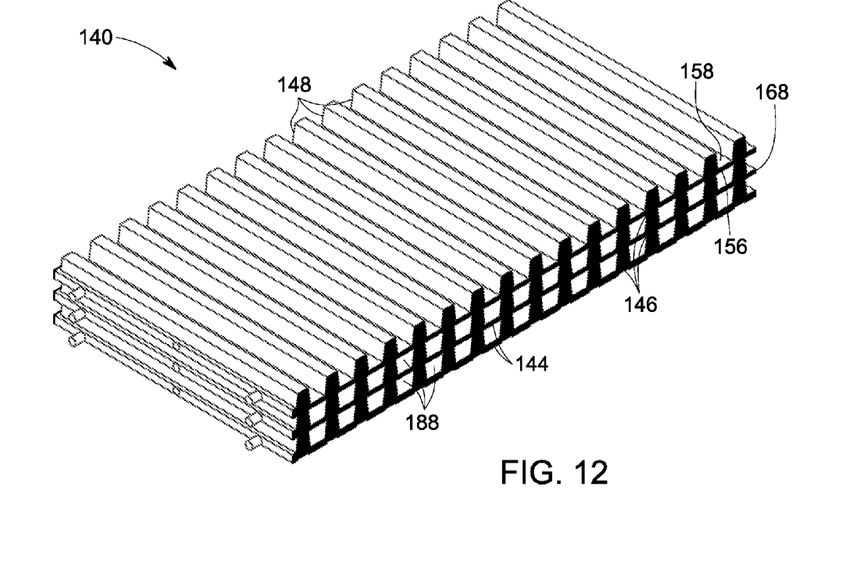
FIG. 12 is a perspective view of a collimator grid in accordance with one exemplary embodiment of the present invention.

FIG. 12 is a perspective view of the collimator grid 140 in accordance with an exemplary embodiment of FIG. 11a. As discussed herein, the collimator grid 140 includes the stacked assembly formed by stacking the plurality of plates 144 one above the other. Each plate 144 in the collimator grid 140 includes the plurality of fins 148 formed on the second surface 158, and the plurality of grooves 146 on the first surface 156 and a blade portion 168.

Figure 13:
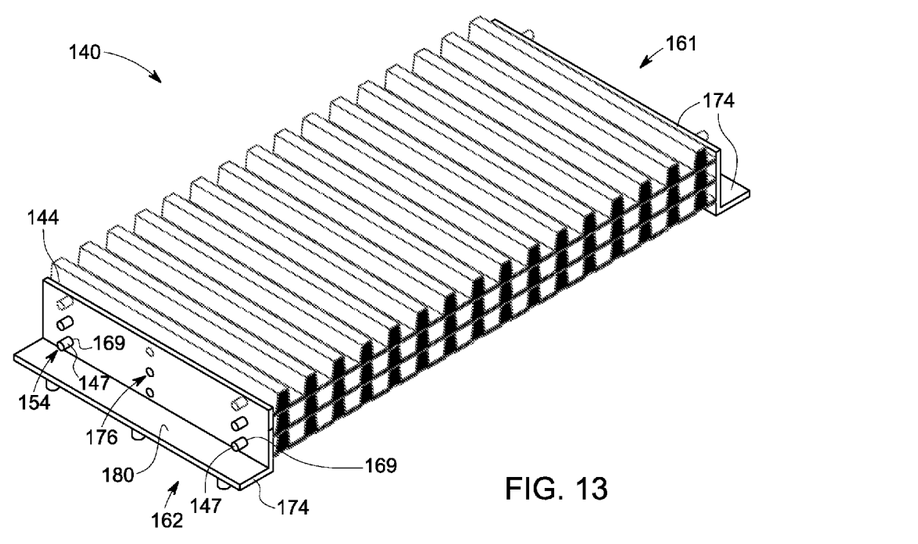
FIG. 13 is a perspective view of a collimator grid coupled to a pair of brackets in accordance with one exemplary embodiment.

FIG. 13 is a perspective view illustrating the pair of brackets 174 coupled to the plurality of plates 144 in the collimator grid 140 in accordance with an exemplary embodiment of FIG. 11b. The pair of mounting brackets 174 are coupled respectively to the second pair of peripheral sides 161, 162 of the plurality of plates 144 of the collimator grid 140. The plurality of third fiducials 176 are interlocked with the plurality of plates 144 via the plurality of second fiducials 154. In other words, protrusions 147 of the plurality of second fiducials 154 are coupled to recesses 169 of the plurality of third fiducials 176 and vice versa. In one embodiment, the mounting plate 180 of the pair of brackets 174 may be used for fitting the collimator grid 140 to the image detector assembly of the CT imaging system. In another embodiment, the pair of brackets 174 may be coupled to the stacked assembly before machining the stacked assembly to remove the plurality of ribs having the plurality of first fiducials from the first pair of the peripheral sides of the plurality of plates 144.

Figure 14:
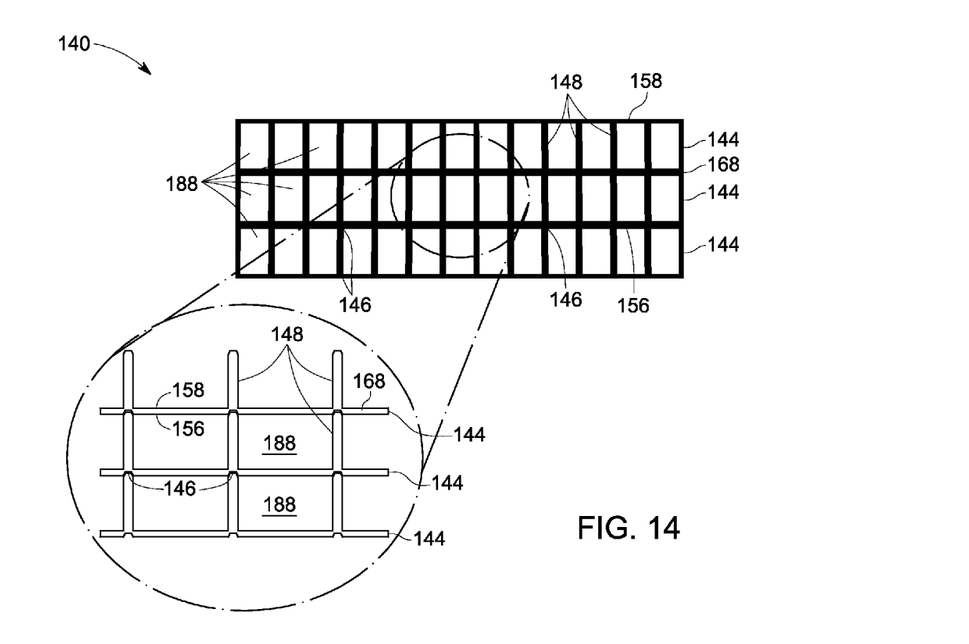
FIG. 14 is a side sectional view of a collimator grid employing the configuration illustrated in FIG. 12 in accordance with one exemplary embodiment of the present invention.

FIG. 14 is a side sectional view of the collimator grid 140 in accordance with an exemplary embodiment of FIG. 12. In the illustrated embodiment, the collimator grid 140 includes three plates 144 stacked one over the other. Each plate includes the plurality of fins 148 extending from the second surface 158 of the blade portion 168 and the plurality of grooves 146 extending from the first surface 156 of the blade portion 168. The plurality of fins 148 of each plate are coupled to the corresponding plurality of grooves 146 of the adjacent plate so as to define the plurality of slits 188.

Each fin 148 may have the same thickness and height as the blade portion 168. In certain other embodiments, the thickness of the plurality of fins 148 may be less than the thickness of the blade portion 168. Length of each fin may have a length in the range of about 0.4 mm to 1.5 mm. Further, the spacing between the fins 148 may be in the range of approximately 0.4 mm to 1.0 mm. Further, in one exemplary embodiment, the height by thickness ratio of the fin 148 may be approximately 80:1.

The inclined orientation of the remaining fins and grooves, and the varied height of the fins facilitate to improve the efficiency of the image detector assembly because the incident x-ray beams are not transmitted parallel, but instead diverge from a point-like focal spot in the x-ray source. Such an effect becomes particularly substantial as the width of the image detector assembly may be greater in the z-direction i.e. the direction in which the medical patient is placed in the CT imaging system. To achieve greater scan areas with better dose efficiency, certain fins among the plurality of fins may be oriented at an angle with respect to the y-axis of the corresponding blade portion. In an exemplary embodiment, the remaining fins among the plurality of fins are oriented towards the focal spot of an x-ray tube (not illustrated) of the x-ray source. The resulting collimator grid is said to be "focally aligned" to the x-ray source. To achieve this overall focal alignment of the fins, the center fins of the collimator grid are oriented along the y-axis and the remaining fins are angled inwards toward the center fins of the collimator grid.

The method of fabricating the collimator grid discussed herein is easy to manufacture as the blade portion and fins of the collimator grid are formed by molding. Stacking the plate's one above the other facilitates easy inspection during assembly of the collimator grid.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method, comprising:
   molding a plurality of plates, each plate having a plurality of grooves formed in a first surface, a plurality of fin tips in a second surface disposed opposite to the first surface, each fin tip aligned with the corresponding groove, a plurality of ribs formed on a first pair of peripheral sides, a plurality of first fiducials spaced apart from each other and formed on the plurality of ribs, and a plurality of second fiducials formed on a second pair of peripheral sides;
   machining the second surface of each plate, between the fin tips, to form the plurality of fins having predefined dimensions;
   stacking the plurality of plates overlapping each other based on the plurality of first fiducials such that the plurality of fins of each plate are coupled to the plurality of grooves of the corresponding adjacent plate; and
   machining the plurality of ribs and the first fiducials to form a collimator grid.

2. The method as set forth in claim 1, wherein forming the plurality of ribs on the first pair of peripheral sides of each plate comprises stiffening each plate.

3. The method as set forth in claim 1, wherein machining the second surface further comprises forming a plurality of recesses on the second surface of each plate such that each recess among the plurality of recesses is formed between the mutually adjacent fins.

4. The method as set forth in claim 1, wherein forming the plurality of fins comprises forming a center fin among the plurality of fins, oriented perpendicular to a blade portion of each plate, and a remaining number of fins oriented perpendicular to the blade portion and, inclined towards the center fin.

5. The method as set forth in claim 1, wherein a height of each fin is increased from one first peripheral side to another first peripheral side among the pair of first peripheral sides.

6. The method as set forth in claim 1, wherein forming the plurality of second fiducials comprises forming at least one of a plurality of recesses, protrusions spaced apart from each other on the second pair of the peripheral sides.

7. The method as set forth in claim 1, further comprising forming a pair of brackets having a plurality of third fiducials comprising at least one of a plurality of recesses, protrusions spaced apart from each other.

8. The method as set forth in claim 7, further comprising coupling the pair of brackets respectively to the second pair of peripheral sides of the stacked plurality of plates.

9. The method as set forth in claim 8, wherein coupling the pair of brackets comprises interlocking the plurality of third fiducials with the plurality of second fiducials.

10. The method as set forth in claim 1, further comprising bonding the plurality of fins of each plate to the plurality of grooves of the corresponding adjacent plate using an adhesive.

11. The method as set forth in claim 1, further comprising bonding the plurality of fins of each plate to the plurality of grooves of the corresponding adjacent plate using a mechanical joining technique.

12. The method as set forth in claim 1, wherein the plurality of first fiducials comprises at least one of a plurality of recesses, protrusions formed on at least one rib surface of each rib.

13. A collimator grid, comprising:
   a plurality of plates stacked overlapping each other, each plate comprising a first surface having a plurality of grooves, and a second surface having a plurality of fins aligned with the plurality of grooves, wherein the plurality of fins of each plate are coupled to the plurality of grooves of the corresponding adjacent plate; wherein the plurality of fins comprises:
      a center fin oriented perpendicular to a blade portion of each plate, and
      a remaining number of fins oriented perpendicular to the blade portion and inclined towards the center fin.

14. The collimator grid as set forth in claim 13, wherein each plate comprises a material including at least one of a tungsten-loaded polymer, a tungsten metal, a tungsten alloy, a molybenum-loaded polymer, a molybdenum metal, a molybdenum alloy, a lead metal, and lead bearing alloy.

15. The collimator grid as set forth in claim 13, further comprising a pair of brackets coupled respectively to a pair of peripheral sides of the stacked plurality of plates via a plurality of fiducials.

16. The collimator grid as set forth in claim 15, wherein the plurality of fiducials comprises at least one of a plurality of recesses, protrusions spaced apart from each other formed on the pair of the peripheral sides of the plurality of plates.

17. The collimator grid as set forth in claim 15, wherein the plurality of fiducials comprises at least one of a plurality of recesses, protrusions spaced apart from each other formed on the pair of brackets.

18. The collimator grid as set forth in claim 15, wherein the plurality of fiducials comprises a plurality of first interlocking fiducials formed on the pair of peripheral sides of the plurality of plates, and a plurality of second interlocking fiducials formed on the pair of brackets, wherein the plurality of first interlocking fiducials is coupled to the corresponding plurality of second interlocking fiducials.

19. The collimator grid as set forth in claim 15, wherein height of each fin is increased from one peripheral side to another peripheral side among another pair of peripheral sides of each plate.

20. A computed tomography imaging system, comprising:
   an x-ray source; and
   an image detector assembly disposed facing the x-ray source, wherein the imaging detector comprises:
      a collimator grid comprising:
         a plurality of plates stacked overlapping each other, each plate comprising a first surface having a plurality of grooves, and a second surface having a plurality of fins aligned with the plurality of grooves, wherein the plurality of fins of each plate are coupled to a plurality of grooves of the corresponding adjacent plate; wherein the plurality of fins comprises:
a center fin oriented perpendicular to a blade portion of each plate, and a remaining number of fins oriented perpendicular to the blade portion and inclined towards the center fin.

21. The computed tomography imaging system as set forth in claim 20, further comprising a pair of brackets coupled respectively to a pair of peripheral sides of the stacked plurality of plates via a plurality of fiducials.

22. The computed tomography imaging system as set forth in claim 21, wherein height of each fin is increased from one peripheral side to another peripheral side among another pair of peripheral sides of the plates.

23. The computed tomography imaging system as set forth in claim 20, wherein the plurality of fins and grooves are configured to focally align with the x-ray source.

\* \* \* \* \*